United States Patent
Guedes et al.

(10) Patent No.: US 10,293,377 B2
(45) Date of Patent: May 21, 2019

(54) MICROMACHINED ULTRASONIC TRANSDUCERS WITH A SLOTTED MEMBRANE STRUCTURE

(71) Applicant: Chirp Microsystems, Berkeley, CA (US)

(72) Inventors: Andre Guedes, Lisbon (PT); David Horsley, Albany, CA (US); Meng-Hsiung Kiang, Albany, CA (US); Richard Przybyla, Berkeley, CA (US); Stefon Shelton, Oakland, CA (US)

(73) Assignee: CHIRP MICROSYSTEMS, Berkeley, CA (US)

( * ) Notice: Subject to any disclaimer, the term of this patent is extended or adjusted under 35 U.S.C. 154(b) by 369 days.

(21) Appl. No.: 15/141,746

(22) Filed: Apr. 28, 2016

(65) Prior Publication Data
US 2017/0021391 A1    Jan. 26, 2017

Related U.S. Application Data

(63) Continuation of application No. PCT/US2015/053605, filed on Oct. 1, 2015.
(Continued)

(51) Int. Cl.
*B06B 1/06* (2006.01)
*B81B 3/00* (2006.01)
(Continued)

(52) U.S. Cl.
CPC .......... *B06B 1/0625* (2013.01); *B06B 1/0603* (2013.01); *B81B 3/00* (2013.01);
(Continued)

(58) Field of Classification Search
CPC ... B06B 1/0625; B06B 1/0629; B06B 1/0633; G01N 29/2437; H01L 41/33; H03H 9/2447
See application file for complete search history.

(56) References Cited

U.S. PATENT DOCUMENTS

| | | |
|---|---|---|
| 4,398,116 A | 8/1983 | Lewis |
| 6,535,612 B1 | 3/2003 | Croft et al. |

(Continued)

FOREIGN PATENT DOCUMENTS

| | | |
|---|---|---|
| DE | 3214789 A1 | 12/1982 |
| EP | 2362686 A2 | 8/2011 |

(Continued)

OTHER PUBLICATIONS

International Search Report and Written Opinion for International Application No. PCT/US15/53605, dated Feb. 5, 2016.
(Continued)

*Primary Examiner* — Bryan P Gordon
(74) *Attorney, Agent, or Firm* — JDI Patent; Joshua D. Isenberg; Robert Pullman (57) ABSTRACT

A piezoelectric micromachined ultrasonic transducer (PMUT) device includes a substrate having an opening therethrough and a membrane attached to the substrate over the opening. A portion of the membrane that overlies the opening is divided into a plurality of cantilevers that are mechanically coupled so that the cantilevers resonate at a common frequency.

48 Claims, 5 Drawing Sheets

Related U.S. Application Data (60) Provisional application No. 62/058,909, filed on Oct. 2, 2014.

(51) Int. Cl.
    *G01N 29/24*     (2006.01)
    *H03H 9/24*     (2006.01)
    *H01L 41/33*     (2013.01)

(52) U.S. Cl.
    CPC ......... *G01N 29/2437* (2013.01); *H01L 41/33* (2013.01); *H03H 9/2447* (2013.01)

(56) References Cited

U.S. PATENT DOCUMENTS

| | | |
|---|---|---|
| 2001/0009587 A1 | 7/2001 | Niederdrank |
| 2005/0130360 A1* | 6/2005 | Zhan ............... B81B 3/0021 438/197 |
| 2005/0215907 A1 | 9/2005 | Toda et al. |
| 2006/0186762 A1* | 8/2006 | Sugiura ............ B06B 1/0692 310/328 |
| 2007/0089516 A1 | 4/2007 | Khuri-Yakub et al. |
| 2012/0053393 A1 | 3/2012 | Kaltenbacher et al. |
| 2012/0250909 A1 | 10/2012 | Grosh et al. |
| 2012/0266675 A1* | 10/2012 | Huffman ............ G01N 29/04 73/632 |
| 2013/0270967 A1 | 10/2013 | Dausch et al. |
| 2015/0323667 A1 | 11/2015 | Przybyla et al. |

FOREIGN PATENT DOCUMENTS

| | | |
|---|---|---|
| EP | 2362686 A3 | 1/2012 |
| EP | 2519030 A1 | 10/2012 |
| JP | S59144997 U | 9/1984 |
| JP | S61150499 A | 7/1986 |
| JP | 2005210172 A | 8/2005 |
| JP | 2011004129 A | 1/2011 |
| WO | 2015131083 A1 | 9/2015 |
| WO | 2016054447 A1 | 4/2016 |

OTHER PUBLICATIONS

U.S. Appl. No. 62/058,909 to Stefon Eric Shelton et al. filed Oct. 2, 2014.

Extended European Search Report dated Apr. 24, 2018 for European Patent Application No. EP15846584.9.

\* cited by examiner

FIG. 1

PRIOR ART

MICROMACHINED ULTRASONIC TRANSDUCERS WITH A SLOTTED MEMBRANE STRUCTURE

CLAIM OF PRIORITY

This application is a continuation of International Patent Application Number PCT/US2015/053605 filed Oct. 1, 2015, the entire contents of which are incorporated herein by reference in their entirety.

International Patent Application Number PCT/US2015/053605 claims the priority benefit of U.S. Provisional Application No. 62/058,909 filed Oct. 2, 2014, the entire contents of which are incorporated herein by reference in their entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

FIELD OF THE DISCLOSURE

The present disclosure generally relates to micromachined ultrasonic transducers (MUTs) and more particularly to a design for a piezoelectric micromachined ultrasonic transducer (PMUT) device and a method to fabricate such a device.

BACKGROUND OF THE DISCLOSURE

The following art appears relevant to the present disclosure:

| U.S. Patent Application Publications | | | |
|---|---|---|---|
| Publication Number | Kind Code | Issue Date | Patentee |
| US2012/0250909 | A1 | Oct. 4, 2012 | Grosh |

Micromachined ultrasonic transducers (MUTs) have been subject to extensive research for the last two decades. Piezoelectric micromachined ultrasonic transducers (pMUTs) are MUTs that use a piezoelectric layer for electromechanical transduction. A typical pMUT is a multilayer membrane structure that is excited into flexural vibration using piezoelectric actuation. The membrane structure is often formed by etching through a silicon wafer to remove the material beneath the membrane, thereby allowing it to vibrate. This etch forms a hollow tube beneath the backside of the membrane. Sound is emitted from the tube when the membrane vibrates, and the tube may be designed as an acoustic resonator to improve acoustic performance of the pMUT. These devices typically operate at the membrane's flexural resonance frequency, which is defined by selecting the correct materials, membrane size, thickness and/or in-plane stress. For multi-pMUT applications, good matching of the resonance frequencies of the individual pMUTs is required for proper operation. For this reason, it is important for pMUTs to be manufactured with closely-matched resonance frequencies. One important parameter causing frequency variation is the residual stress present in the layers composing the pMUT membrane, in particular in the piezoelectric layer. A typical pMUT structure consists of a membrane that is attached to the substrate at its boundary, a condition that is described as a clamped boundary condition. The resonant frequency of a membrane with a clamped boundary condition is very sensitive to in-plane residual stress. Several designs have been suggested to reduce stress sensitivity, such as released cantilevers and flexurally-suspended membranes, but they all show poor acoustic performance and or poor manufacturability (e.g. inefficient resonance modes, cracks created by stress concentrations, poor micro-fabrication yield)

In US 2012/0250909 Grosh describes an acoustic transducer wherein a membrane transducer is released from the substrate by separating the membrane into several identical tapered cantilevers, reducing the effect of stress on the mechanical behavior of the membrane. Grosh's approach works well for a non-resonant device, such as a conventional piezoelectric microphone. However, for a pMUT operated at resonance, small differences caused by fabrication variations can cause the cantilevers to have slightly different resonance frequencies, resulting in considerable negative impact on the acoustic performance of the device when operated at resonance. Specifically, when excited at a single frequency, mismatched cantilevers will oscillate with significantly different phase and amplitude, creating phase and amplitude errors in the ultrasound signal.

Accordingly, what is needed is a pMUT design with good acoustic performance that resonates at a single stable resonance mode, and with low sensitivity to stress. This invention describes such design.

SUMMARY

According to aspects of this disclosure a piezoelectric micromachined ultrasonic transducer (PMUT) device may include a clamped membrane in any symmetric shape (circular, squared, triangular, among others) that is partially released by "slicing" the membrane into cantilevers, which may include two or more tapered and/or identically-shaped cantilevers. The individual cantilevers are mechanically coupled so that they resonate together at the same frequency, thereby avoiding the multiple resonant frequencies that occur with individually-defined cantilevers having small dimension variations. When compared to a fully clamped membrane, this design shows the following advantages: (i) reduced stress sensitivity; (ii) increased transmit and receive acoustic sensitivity, coming from the fact that the released design enables larger displacement of the membrane; (iii) resonance frequency adjustment—the resonance frequency of the device can be easily adjusted by defining the number of slices that comprise the structure, as well as the number of connections between slices. This feature is extremely advantageous since the resonance frequency can be adjusted without changing the basic dimensions of the membrane, such as diameter and thickness.

BRIEF DESCRIPTION OF THE FIGURES

The present disclosure may be better understood by reference to the following drawings which are for illustrative purposes only.

DETAILED DESCRIPTION

Although the description herein contains many details, these should not be construed as limiting the scope of the invention but as merely providing illustrations of some of the presently preferred embodiments of this invention. Therefore, it will be appreciated that the scope of the present invention fully encompasses other embodiments, which may become obvious to those skilled in the art.

Aspects of this disclosure include a micromachined ultrasonic transducer (MUT), in particular a piezoelectric micromachined ultrasonic transducer (pMUT) device comprising a circular membrane, sliced in identical tapered cantilevers anchored at the perimeter of the membrane. The cantilevers are mechanically coupled; in one embodiment the coupling may be accomplished using several concentric rings. It will be appreciated that the following embodiments are provided by way of example only, and that numerous variations and modifications are possible. For example, while circular embodiments are shown, the pMUT membrane may have many different shapes such as square, rectangular, hexagonal, octagonal, and so on. Furthermore, while pMUTs are shown in this description, other MUTs should also be considered, such as capacitive micromachined ultrasonic transducers (cMUTs) or optical acoustic transducers. Also, although this description is focused on pMUTs having a unimorph construction, consisting of a single piezoelectric layer on a passive layer, aspects of the disclosure are not limited thereby. For example, bimorph and multimorph pMUTs having multiple piezoelectric layers and various electrode patterns are possible, and should also be considered part of the present disclosure. All such variations that would be apparent to one of ordinary skill in the art are intended to fall within the scope of this disclosure. It will also be appreciated that the drawings are not necessarily to scale, with emphasis being instead on the distinguishing features of the bonded wafer pMUT device disclosed herein.

Figure 1:
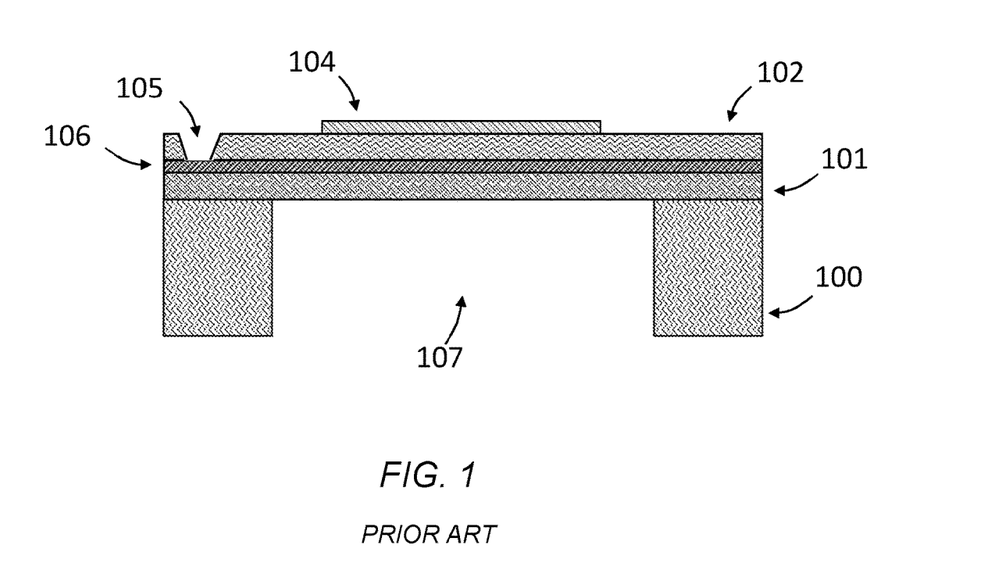
FIG. 1 shows a cross section of a circular clamped transducer design known from prior art.
Figure 2:
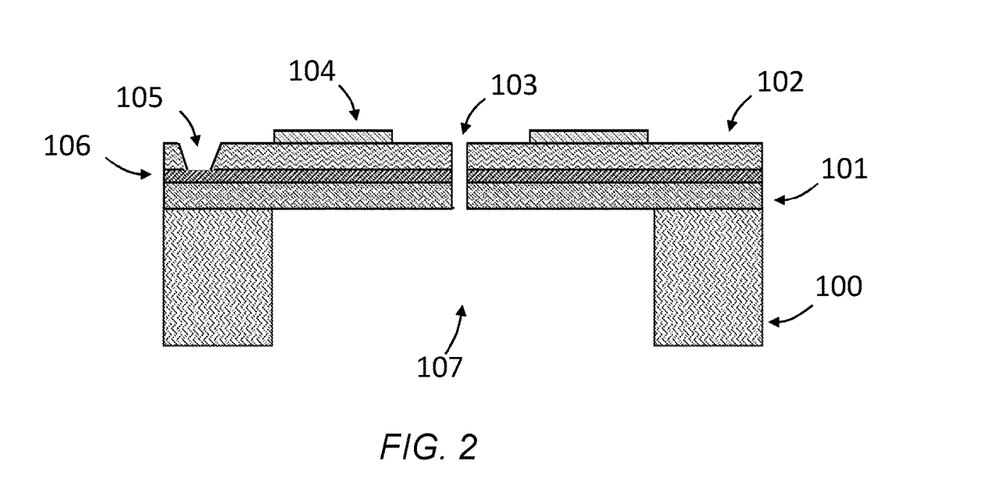
FIG. 2 is a cross section of a circular embodiment of the proposed partially released pMUT.
Figure 3:
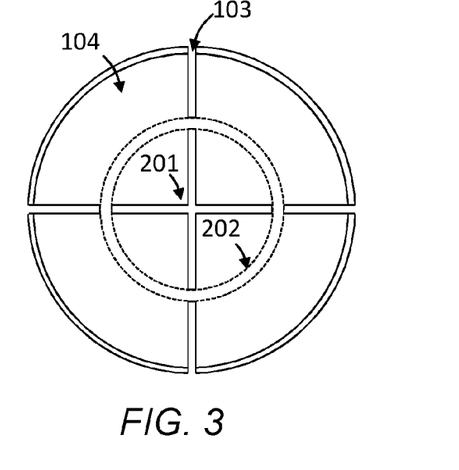
FIG. 3 is a top view of the proposed pMUT, showing a 4 slice design, with one connecting ring (highlighted).

FIG. 2 is a cross-section illustration of the proposed pMUT formed from multiple thin-film layers deposited onto the substrate 100. Substrate 100 may be silicon but alternative materials such as glass or polymer substrates may be used. In the unimorph pMUT construction illustrated here as one embodiment, a passive layer 101 is first deposited onto the substrate 100. Passive layer 101 may be composed of various materials such as silicon, silicon oxide, and/or silicon nitride, and the thickness of this layer is in the range of 0.5 microns to 30 microns for transducers with center frequency from 40 kHz to 20 MHz, and more specifically from 1 micron to 10 microns for transducers with center frequency from 40 kHz to 1 MHz. A conductive metal bottom electrode layer 106 is then deposited. Bottom electrode 106 can be patterned or not, and may be composed of various metals such as Mo, Pt, or Al, and the thickness of this layer is from 50 nm to 400 nm and more specifically from 100 nm to 300 nm. Piezoelectric layer 102 may be composed of various piezoelectric materials including AlN, PZT (lead zirconate titanate), ZnO, KNN ($K_xNa_{1-x}NbO_3$) or PMN-PT (lead magnesium niobate-lead titanate). Polymer piezoelectric materials such as PVDF may be used as piezoelectric layer 102 as well. The thickness of piezoelectric layer 122 is from 250 nm to 3000 nm, and more specifically from 500 nm to 1500 nm. A conductive top electrode metal layer 104 is then deposited. Various metals may be used for top electrode 104, including Al, Au, Cu, and Mo. The thickness of top electrode 104 is from 50 nm to 3000 nm and more specifically from 100 nm to 1000 nm. Electrical contact to the bottom electrode metal 106 is formed by etching a via 105 through the piezoelectric layer 102. The multilayer membrane is then etched to form identical tapered cantilevers anchored at the perimeter of the membrane. The cantilevers are mechanically coupled to ensure that they resonate at a common frequency. In one embodiment, this coupling is achieved by one or more concentric rings connecting the cantilevers. The gap 103 should be smaller than $(1 \mu m)/f_o$, where $f_o$ is the operational frequency in MHz, or more specifically smaller than $(0.6 \mu m)/f_o$. The gap 103, the concentric ring connection 202, and partially released pMUT triangular cantilevers can be better understood from top view FIG. 3. The number of cantilever slices can be defined to target a specific acoustic performance and resonance frequency. The final pMUT structure is formed by releasing the membrane from the substrate 100. In one embodiment, the release etch is performed by etching through the back of the wafer, forming an opening 107, e.g., a tube, through backside of the substrate 100. When a silicon substrate is employed, this etch may be conducted by deep reactive ion etching (DRIE). Alternative fabrication methods using front-side etching to release the membrane are also possible. The membrane diameter is in the range of 100 microns to 2000 microns for transducers operating at frequencies from 40 kHz to 10 MHz and more specifically the diameter is from 200 microns to 1500 microns for transducers operating at frequencies from 60 kHz to 600 kHz. The etch may be performed after thinning the substrate 100 by grinding or other means. The thickness of the substrate 100 may be determined such that the opening 107 possesses an acoustic resonance frequency that is matched to the center frequency of the PMUT.

Figure 4:
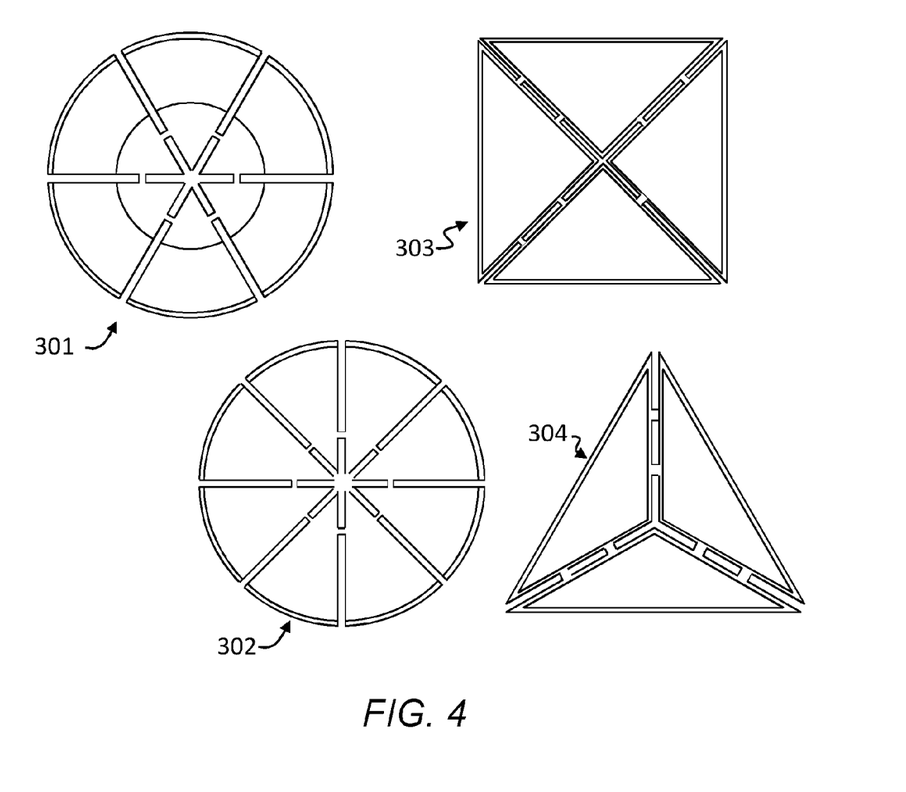
FIG. 4 is a top view of different alternative embodiments with different shapes, comprising different number of partially released cantilevers: 4, 6 and 8.

FIG. 4 shows alternative embodiments, representing circular membranes with different numbers of connecting rings and partially released cantilevers 301-302, and also membranes with alternative shaped geometries in particular a triangular 304, and a square 303 design.

Figure 5A:
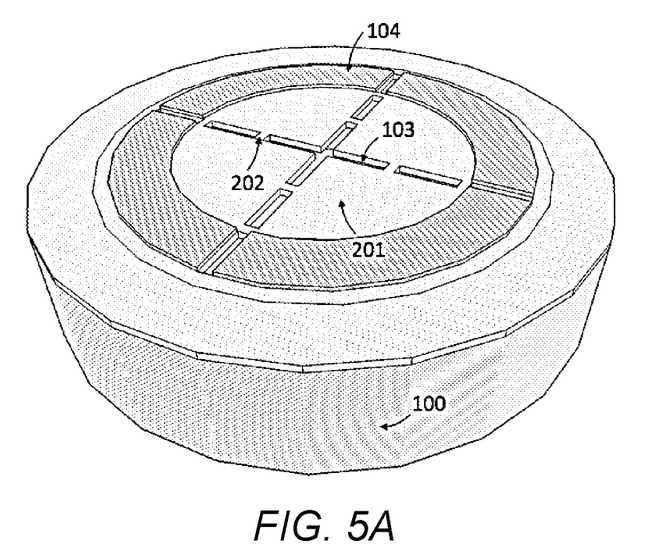
FIG. 5(a) shows a full isometric view of the pMUT circular embodiment.
Figure 5B:
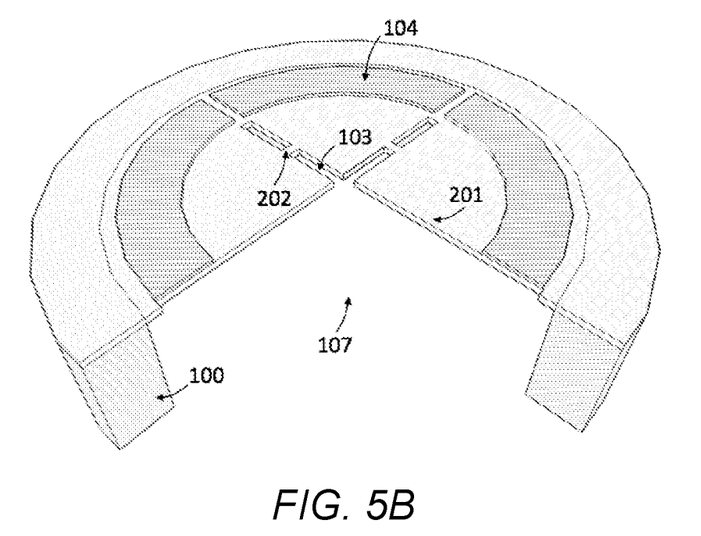
FIG. 5(b) shows the same isometric view of the embodiment, with an open cut section for better viewing and understanding of the pMUT structure and geometry.

FIG. 5(a) shows a full isometric view of the pMUT circular embodiment. FIG. 5(b) shows the same isometric view of the embodiment, with an open cut section for better viewing and understanding of the pMUT structure and geometry.

Figure 6:
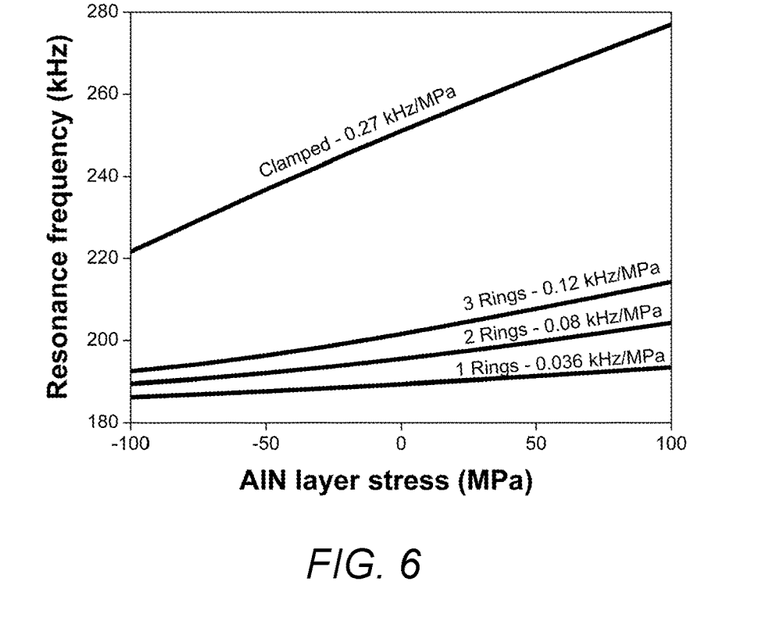
FIG. 6 Comparison of the stress sensitivity of a fully clamped pMUT membrane, and the proposed pMUT design comprising different number of cantilever slices and connecting rings.

By partially etching the gaps 103 to define the suspended cantilevers in the membrane, the stress sensitivity is largely reduced. The in-plane stress present in the pMUT structural layers is released due to the less constrained geometry of the released cantilevers. The stress release has an effect on the initial static deformation of the pMUT, which will deform up or downwards, depending on the average residual stress and residual stress gradients present in the layers. Finite element method (FEM) simulations were conducted to model the resonance frequency of several pMUT designs at varying levels of residual stress in the piezoelectric layer. FIG. 6 compares resonance frequency as a function of residual stress for the standard clamped design, and three preferred pMUT embodiments with four, six and eight partially released cantilevers. For this example the following pMUT structure was considered: top electrode (104)—aluminum (0.2 μm)/piezoelectric layer (102)—aluminum nitride (1 μm)/bottom electrode (106)—molybdenum (0.2 μm)/passive layer (101)—silicon (4 μm). Membrane diameter—600 μm/gap (103) 4 μm. Connecting rings width—4 μm.

Figure 7:
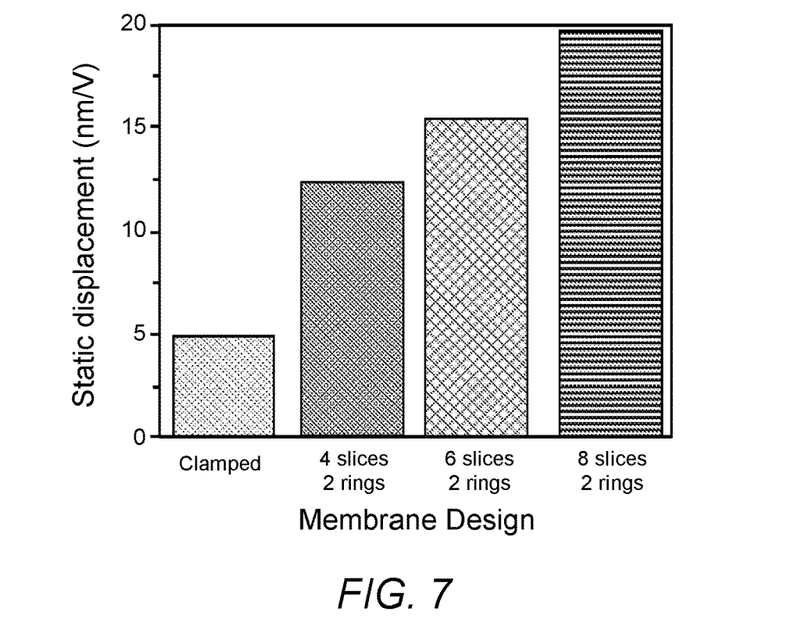
FIG. 7 shows a comparison of the static displacement in nm/V of a standard clamped pMUT membrane, and the proposed pMUT design comprising 4, 6 and 8 slices/cantilevers all with two connecting rings.

The preferred pMUT embodiment also has advantages in terms of maximum displacement and acoustic performance in both transmitter and receiver mode, when compared to a fully clamped membrane. When driven at resonance, the mechanical nature of a cantilever beam allows it to displace much more than a constrained or fully clamped membrane structure. By way of example, and not of limitation, FIG. 7 shows the results of FEM simulation of the static displacement per unit volt of a standard fully clamped circular pMUT, and the proposed slotted pMUT with similar dimensions. This enhancement in displacement directly translates to augmented output pressure.

Figure 8:
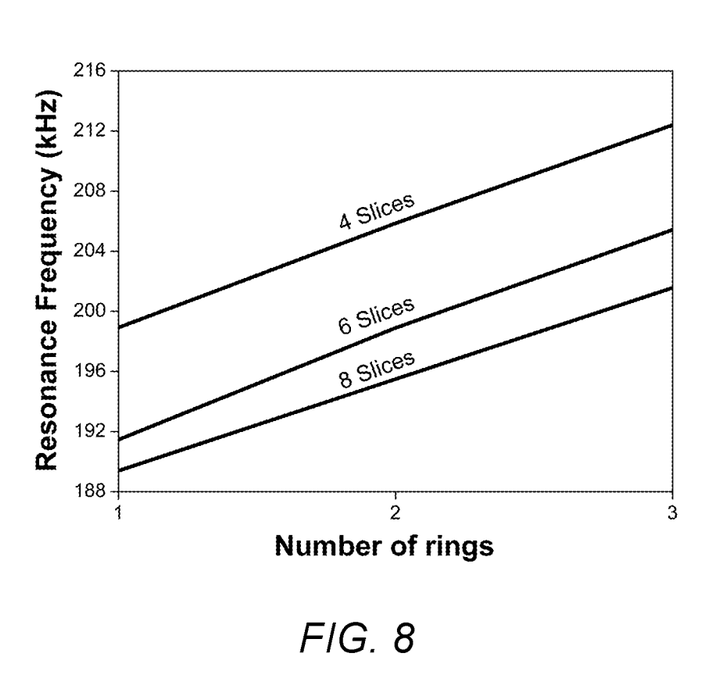
FIG. 8 Resonance frequencies for similar pMUT embodiments with different number of released cantilevers, and connecting rings.

The number of slices/cantilevers and the number of ring connectors that mechanically couple the cantilevers together can be used to adjust the resonance frequency of the structure without changing its basic dimensions such as the thickness of the layers and/or the diameter of the membrane. By way of example, and not of limitation, FIG. 8 shows the results of FEM simulations of resonance frequency for pMUTs having various numbers of sliced cantilevers and ring connectors in the membrane for the following structure: top electrode (104)—aluminum (0.2 μm)/piezoelectric layer (102)—aluminum nitride (1 μm)/bottom electrode (106)—molybdenum (0.2 μm)/passive layer (101)—silicon (4 μm). Membrane diameter—600 μm/gap (103)—4 μm. Connecting rings width—4 μm. As seen in FIG. 8, the resonance frequency decreases with the number of slices and rings, and for this particular example, the frequency can be adjusted in a range of 23 kHz (189 to 212 kHz).

All cited references are incorporated herein by reference in their entirety. In addition to any other claims, the applicant(s)/inventor(s) claim each and every embodiment of the invention described herein, as well as any aspect, component, or element of any embodiment described herein, and any combination of aspects, components or elements of any embodiment described herein.

The appended claims are not to be interpreted as including means-plus-function limitations, unless such a limitation is explicitly recited in a given claim using the phrase "means for." Any element in a claim that does not explicitly state "means for" performing a specified function, is not to be interpreted as a "means" or "step" clause as specified in 35 USC § 112, § 6. In particular, the use of "step of" in the claims herein is not intended to invoke the provisions of 35 USC § 112, § 6.

What is claimed is:

1. A piezoelectric micromachined ultrasonic transducer (PMUT) device, comprising:
    a substrate having an open cavity; and
    a membrane attached to the substrate over the opening, a portion of the membrane that overlies the open cavity being divided into a plurality of cantilevers wherein the cantilevers are mechanically coupled by one or more interruptions in gaps between adjacent cantilevers so that the cantilevers resonate at a common frequency, wherein the one or more interruptions are located between a perimeter of the open cavity and a center of the open cavity.

2. The device of claim 1, wherein the open cavity is fully open through the substrate from a side of the substrate to which the membrane is attached to a side of the substrate opposite the side of the substrate to which the membrane is attached.

3. The device of claim 1, wherein the cavity is partially open from a side of the substrate to which the membrane is attached but not through to a side of the substrate opposite the side of the substrate to which the membrane is attached.

4. The device of claim 1, wherein a shape of the membrane is a circular shape.

5. The device of claim 1, wherein a shape of the membrane is a squared shape.

6. The device of claim 1, wherein a shape of the membrane is a triangular shape.

7. The device of claim 1, wherein the plurality of cantilevers includes two or more cantilevers.

8. The device of claim 1, wherein the plurality of cantilevers includes three or more cantilevers.

9. The device of claim 1, wherein the plurality of cantilevers includes four or more cantilevers.

10. The device of claim 1, wherein the plurality of cantilevers includes six or more cantilevers.

11. The device of claim 1, wherein the plurality of cantilevers includes eight or more cantilevers.

12. The device of claim 1, wherein the plurality of cantilevers includes two or more identically-shaped cantilevers.

13. The device of claim 1, wherein the plurality of cantilevers includes two or more tapered cantilevers.

14. The device of claim 1, wherein the plurality of cantilevers includes two or more identically-shaped tapered cantilevers.

15. The device of claim 1, wherein a thickness of the substrate is such that an acoustic resonance frequency of the opening is approximately equal to the common frequency.

16. The device of claim 1, wherein the membrane includes multiple layers of material.

17. The device of claim 16, wherein the multiple layers include a passive layer formed on the substrate.

18. The device of claim 17, wherein the multiple layers further include a conductive bottom electrode layer formed on the passive layer.

19. The device of claim 18, wherein the multiple layers further include a piezoelectric layer formed on the conductive bottom electrode layer.

20. The device of claim 19, wherein the multiple layers further include a conductive top electrode layer formed on the piezoelectric layer.

21. The device of claim 1, wherein the cantilevers are mechanically coupled by one or more concentric rings.

22. The device of claim 1, wherein the cantilevers are mechanically coupled by two or more concentric rings.

23. The device of claim 1, wherein the cantilevers are mechanically coupled by three or more concentric rings.

24. The device of claim 1, wherein a gap between adjacent cantilevers of the plurality is smaller than $(1\ \mu m)/f_o$, where $f_o$ is an operational frequency of the device in MHz.

25. The device of claim 24, wherein the gap is smaller than $(0.6\ \mu m)/f_o$.

26. A method for fabricating a piezoelectric micromachined ultrasonic transducer (PMUT) device, comprising:
    forming a membrane attached to a substrate;
    dividing a portion of the membrane into a plurality of cantilevers that are mechanically coupled; and
    forming an opening through a portion of the substrate underling the plurality of cantilevers to release the cantilevers, wherein the cantilevers are mechanically coupled by one or more interruptions in gaps between adjacent cantilevers so that the cantilevers resonate at a common frequency, wherein the one or more interruptions are located between a perimeter of the open cavity and a center of the open cavity.

27. The method of claim 26, wherein a shape of the membrane is a circular shape.

28. The method of claim 26, wherein a shape of the membrane is a squared shape.

29. The method of claim 26, wherein a shape of the membrane is a triangular shape.

30. The method of claim 26, wherein the plurality of identically-shaped tapered cantilevers includes two or more cantilevers.

31. The method of claim 26, wherein the plurality of cantilevers includes three or more cantilevers.

32. The method of claim 26, wherein the plurality of cantilevers includes four or more cantilevers.

33. The method of claim 26, wherein the plurality of cantilevers includes six or more cantilevers.

34. The method of claim 26, wherein the plurality of cantilevers includes eight or more cantilevers.

35. The method of claim 26, wherein the plurality of cantilevers includes two or more identically-shaped cantilevers.

36. The method of claim 26, wherein the plurality of cantilevers includes two or more tapered cantilevers.

37. The method of claim 26, wherein the plurality of cantilevers includes two or more identically-shaped tapered cantilevers.

38. The method of claim 26, wherein a thickness of the substrate is such that an acoustic resonance frequency of the opening is approximately equal to the common frequency.

39. The method of claim 26, wherein forming the membrane includes forming multiple layers of material.

40. The method of claim 39, wherein forming the multiple layers includes forming a passive layer on the substrate.

41. The method of claim 40, wherein forming the multiple layers further includes forming a conductive bottom electrode layer on the passive layer.

42. The method of claim 41, wherein forming the multiple layers further includes forming a piezoelectric layer on the conductive bottom electrode layer.

43. The method of claim 42, wherein forming the multiple layers further includes forming a conductive top electrode layer on the piezoelectric layer.

44. The method of claim 26, wherein dividing a portion of the membrane into a plurality of identically-shaped tapered cantilevers that are mechanically coupled includes forming one or more concentric rings that couple the identically-shaped tapered cantilevers.

45. The device of claim 44, wherein forming the one or more concentric rings includes forming two or more concentric rings.

46. The device of claim 44, wherein forming the one or more concentric rings includes forming three or more concentric rings.

47. The method of claim 26, wherein dividing a portion of the membrane into a plurality of identically-shaped tapered cantilevers that are mechanically coupled includes forming a gap between adjacent cantilevers of the plurality, wherein the gap is smaller than $(1\ \mu m)/f_o$, where $f_o$ is an operational frequency of the device in MHz.

48. The method of claim 47, wherein the gap is smaller than $(0.6\ \mu m)/f_o$.

* * * * *